US006506313B1

(12) United States Patent
Fetterman et al.

(10) Patent No.: US 6,506,313 B1
(45) Date of Patent: Jan. 14, 2003

(54) ULTRAMINIATURE FIBER OPTIC PRESSURE TRANSDUCER AND METHOD OF FABRICATION

(75) Inventors: Harold R. Fetterman, Pacific Palisades, CA (US); Leonid Bukshpun, West Hollywood, CA (US); Joseph Michael, Los Angeles, CA (US)

(73) Assignee: Pacific Wave Industries, Inc., Los Angeles, CA (US)

( * ) Notice: Subject to any disclaimer, the term of this patent is extended or adjusted under 35 U.S.C. 154(b) by 0 days.

(21) Appl. No.: 09/495,983

(22) Filed: Feb. 1, 2000

(51) Int. Cl.$^7$ .............................................. B29D 11/00
(52) U.S. Cl. ............................................ 216/24; 385/12
(58) Field of Search ............................... 216/24; 385/12

(56) References Cited

U.S. PATENT DOCUMENTS

| | | | |
|---|---|---|---|
| 4,711,246 A | 12/1987 | Alderson | 128/667 |
| 4,787,396 A | 11/1988 | Pidorenko | 128/667 |
| 5,085,223 A | 2/1992 | Lars et al. | 128/675 |
| 5,313,957 A | 5/1994 | Little | 128/748 |
| 5,316,619 A * | 5/1994 | Mastrangelo | 438/53 |
| 5,365,789 A * | 11/1994 | Totterdell et al. | 73/705 |
| 5,438,873 A | 8/1995 | Wlodarczyk et al. | 73/705 |
| 5,841,131 A * | 11/1998 | Schroeder et al. | 250/227.14 |
| 5,936,164 A * | 8/1999 | Sparks et al. | 73/724 |

OTHER PUBLICATIONS

O. Tohyama, M. Kohashi, M. Fukui and H. Itoh, "A Fiber–Optic Pressure Microsensor for Biomedical Applications", *Transducers '97* (1997 International Conference on Solid–State Sensors and Actuators, Chicago, Jun. 16–19, 1997, pp. 1489–1492).

H. Lorenz, M. Despont, N. Fahrni, N. LaBianca, P. Renaud and P. Vettiger, "SU–8: a low–cost negative resist for MEMS", *J. Micromech. Microeng.* 7(1997), pp. 121–124.

* cited by examiner

*Primary Examiner*—Benjamin L. Utech
*Assistant Examiner*—Shamin Ahmed
(74) *Attorney, Agent, or Firm*—Henricks, Slavin & Holmes LLP

(57) ABSTRACT

A method of batch fabrication of ultraminiature fiber optic pressure transducers including the steps of: providing a first substrate with a first sacrificial layer formed thereover; forming a plurality of light reflective diaphragm structures on the first sacrificial layer; forming a plurality of fiber stopper structures on the light reflective diaphragm structures; forming a plurality of fiber alignment cavity structures on the fiber stopper structures, the light reflective diaphragm structures, fiber stopper structures and fiber alignment cavity structures providing a plurality of fiber alignment assemblies; providing a second substrate with a second sacrificial layer formed thereover; forming a plurality of ferrule structures over the second sacrificial layer; inputting a plurality of fibers into the ferrule structures and sealing each of the ferrule structures to the fiber inserted therein, the ferrule structures and the fibers providing a plurality of fiber-ferrule assemblies; etching the second sacrificial layer releasing the fiber-ferrule assemblies; inputting the fiber-ferrule assemblies into the fiber alignment assemblies and sealing each of the fiber alignment assemblies to the fiber-ferrule assembly inserted therein, the fiber alignment assemblies and the fiber-ferrule assemblies providing a plurality of fiber optic pressure transducers; and etching the first sacrificial layer releasing the fiber optic pressure transducers.

12 Claims, 4 Drawing Sheets

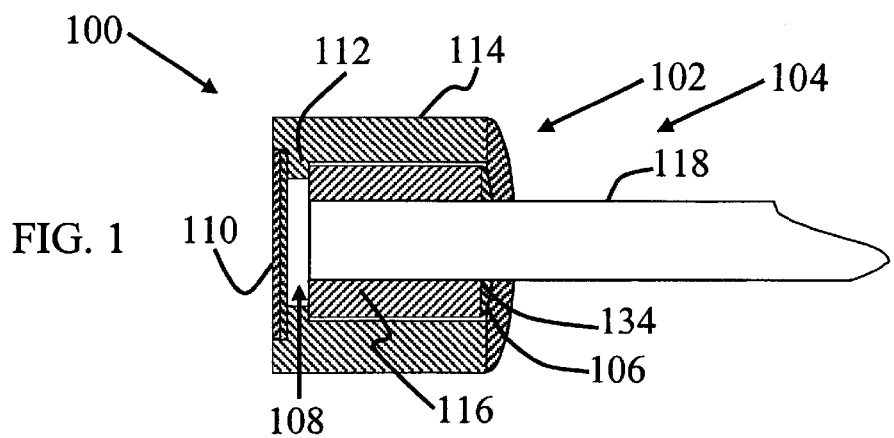
FIG. 1
FIG. 2
FIG. 3
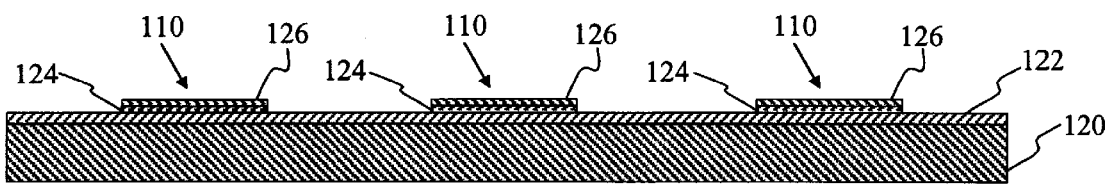
FIG. 4
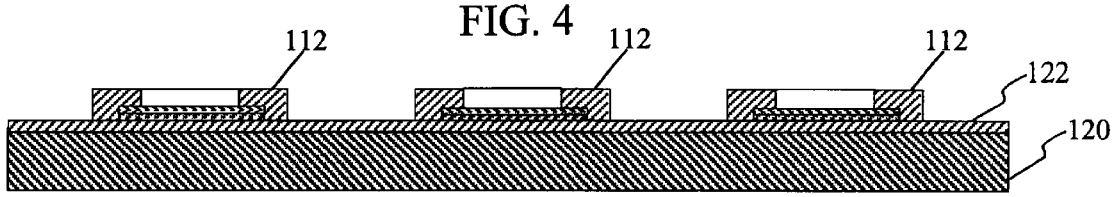
FIG. 5
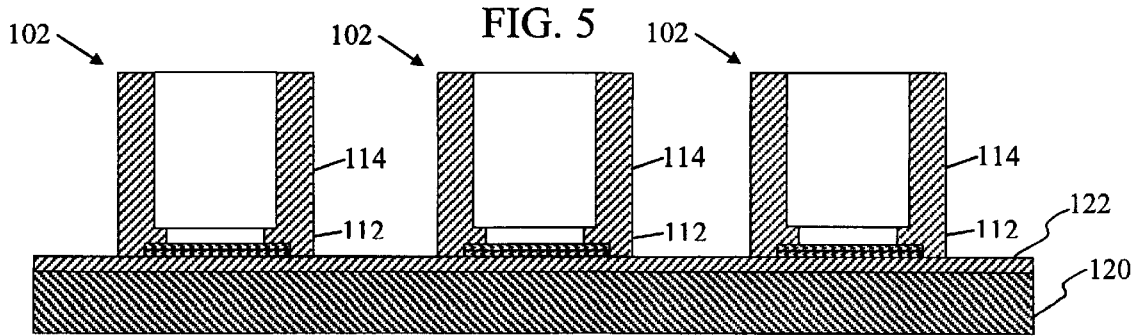

ULTRAMINIATURE FIBER OPTIC PRESSURE TRANSDUCER AND METHOD OF FABRICATION

BACKGROUND OF THE INVENTION

1. Field of Invention

The present invention relates generally to fiber optic coupled pressure transducers and methods for their fabrication and, more particularly, to ultraminiature fiber optic pressure transducers formed with a photosensitive polymer and a micromachining technique for fabricating the same.

2. Description of the Related Art

Light intensity modulated transducers employ measurements of changes in a light signal sent to and reflected back from a moving reflective surface. In the case of fiber optic pressure transducers, light from an optical source, e.g., a light emitting diode, is transmitted through an optical fiber to a light reflective diaphragm at the fiber tip, and reflected back from the reflective diaphragm through the same fiber to a light level analysis unit. Generally, the amount of light that is reflected is determined by the distance between the reflective diaphragm and the fiber end. As the pressure on the diaphragm changes, its reflective surface is deflected toward or away from the fiber end changing the amount of reflected light in accordance with the applied pressure.

An example of such a fiber optic pressure transducer is provided in U.S. Pat. No. 4,787,396 to Pidorenko, the entirety of which is incorporated herein by reference. The disclosed pressure transducer incorporates four structural members: a fiber, a fiber-holding ferrule with an annular shoulder, a cylindrical cap with a rounded lip, and a light reflective diaphragm. The ferrule is formed from continuous, cylindrical, drawn titanium tubing which is fed through a screw machine where it is turned, a step is cut in the end to provide the annular shoulder, and then cut to length. The cap is formed from a titanium rod and drilled and bored to provide a step for the diaphragm. In the disclosed pressure transducer, the diaphragm is permanently affixed between the lip of the cap and the annular shoulder of the ferrule, at a fixed distance from the end of the fiber-ferrule assembly.

Another example of a fiber optic pressure transducer and method of fabrication is provided in U.S. Pat. No. 4,711,246 to Alderson, the entirety of which is incorporated herein by reference. The disclosed pressure transducer includes: a hollow cylindrical cap made from titanium with a diaphragm formed to its final thickness and shape by a hot coining process, and a ferrule made from drawn tubing. In the disclosed method, the ferrules are cut and loaded into a fixture plate, and then fibers are inserted into the ferrules. The plate, including the end surfaces of the ferrules and fibers, is lapped and polished in a single operation. A photoresist coating is applied to the fiber ends. A pattern of small holes is made in the resist material via exposure in a standard semiconductor alignment machine. Then, the ferrules are unloaded from the machine and ready for assembly with the caps.

A problem with the above techniques is that the structural members are fabricated separately using conventional machining. Thus, completed transducers are about 1 mm and larger in size. Moreover, the manual assembly of such structural members can be costly.

In "A Fiber-Optic Pressure Microsensor for Biomedical Applications" by O. Tohyama, M. Kohashi, M. Fukui and H. Itoh in *TRANSDUCERS* '97 (1997 International Conference on Solid-State Sensors and Actuators, Chicago, Jun. 16–19, 1997, pp. 1489–92), the entirety of which is incorporated herein by reference, an intensity modulated fiber optic pressure sensor including separately processed silicon wafers (diaphragm, fiber stopper and alignment structure) is disclosed. The silicon wafers are bonded together and then diced to provide individual sensing elements.

A problem with the Tohyama technique is that using wafer dicing to separate the individual sensing elements for attaching each of the sensing elements to a fiber is a costly manufacturing process. Moreover, the Tohyama technique requires complex separated processing steps, a complicated alignment procedure and special handling, thus increasing the cost and reducing the fabrication yield. Although the Toyama article discloses a completed sensing element with an outer diameter of 270 $\mu$m, its sensitivity is limited by its relatively thick (50 $\mu$m) fiber stopper.

Fiber optic pressure transducers hold great potential in a variety of applications for direct, accurate measurements of pressure in gases and liquids because of their wide dynamic range, high sensitivity, and an immunity to electromagnetic influence. To be successfully used in medical applications that require pressure measurements in human organs, the transducers should be made as small as possible to be inserted through small catheters and infusion needles to minimize the painfulness of medical routines. For clinical routines, it would also be very desirable for transducers to be disposable.

Thus, there is a need for a simple and reliable, low cost, batch in nature fabrication process for fiber optic pressure transducers which includes a small number of processing steps and does not require individual handling of parts during fabrication.

There is also a need to improve the sensitivity of fiber optic pressure transducers such that a single mode fiber with a core, for example, of 4–10 $\mu$m, could be utilized with a comparable fiber-diaphragm distance.

SUMMARY OF THE INVENTION

The present invention is embodied in an "ultraminiature" fiber optic pressure transducer which is suitable for a variety of medical applications including, but not limited to, treating pressure build-up in kidneys and high blood pressure. The term "ultraminiature" means sufficiently small in size (about 350 $\mu$m and smaller) to be inserted by a needle into the body so that, when the needle is withdrawn, the body can heal without the need for stitches, sutures or the like.

An exemplary preferred embodiment of the present invention generally relates to an ultraminiature, high sensitivity fiber optic pressure transducer structure and a batch method for fabricating the same. The pressure transducer includes a fiber-ferrule assembly and a fiber alignment assembly sized to receive the fiber-ferrule assembly. The fiber alignment (and pressure sensing) assembly includes an integrally formed diaphragm, fiber stopper and fiber alignment cavity. The fiber-ferrule assembly includes a fiber and a ferrule sized to receive the fiber therein. In an exemplary preferred embodiment, the structural members of the pressure transducer are formed with a photosensitive polymer such as an epoxy-based photoresist which provides precise alignment structures which are rigid or hard and facilitates easy and accurate fitting of the fiber-ferrule assemblies into the fiber alignment assemblies.

According to the present invention, the structural members are made by using an entirely surface micromachining technique. Completed free standing pressure sensing elements are formed on the surface of a substrate simultaneously, and then released therefrom. The fabrication method of the present invention eliminates manual handling of micro parts during the fiber assembling and releasing processes.

In an exemplary preferred method, the fiber alignment (and pressure sensing) assemblies are formed on a first substrate and the fiber-ferrule assemblies are formed on a second substrate. The structural members are formed onto the first substrate in series, one after another: the light reflective diaphragms and then the fiber stoppers and fiber alignment structures. The reflective diaphragms are formed with any desired thickness. Ferrule structures are formed onto the second substrate and then fibers are inserted into and sealed to the ferrule structures forming the fiber-ferrule assemblies. The fiber-ferrule assemblies are released from the second substrate and inserted into and sealed to the fiber alignment assemblies. The fiber alignment assemblies remain secured to the first substrate until completed transducers are to be freed therefrom. As a result of this process flow, all monolithic sensing elements are ready at the same time.

A method for making an ultraminiature fiber optic pressure transducer integrally composed of photosensitive polymer members, and a single mode fiber, in accordance with one embodiment of the present invention, includes the steps of: forming a sacrificial layer on a surface of a substrate; forming flexible light reflective diaphragms on the sacrificial layer; forming fiber stopper structures on the surface of the substrate, the fiber stopper structures being in alignment with the diaphragms; forming fiber alignment structures on the fiber stopper structures, the fiber alignment structures being in alignment with the diaphragms and the fiber stopper structures, the diaphragms, the fiber stopper structures and the fiber alignment structures serving as pressure sensing elements; forming a sacrificial layer on a surface of an additional substrate; forming ferrule structures on the surface of the additional substrate; inputting fibers into the ferrule structures including sealing the ferrules to the fibers, the ferrule structures and the fibers serving as fiber-ferrule assemblies; etching the sacrificial layer to release the fiber-ferrule assemblies from the additional substrate; inputting the fiber-ferrule assemblies into the pressure sensing elements including sealing the pressure sensing elements to the fiber-ferrule assemblies, the pressure sensing elements and the fiber-ferrule assemblies serving as fiber optic pressure transducers; and etching the sacrificial layer to release the fiber optic pressure transducers from the substrate.

A method of batch fabrication of ultraminiature fiber optic pressure transducers in accordance with another embodiment of the present invention includes the steps of: providing a first substrate with a first sacrificial layer formed thereover; forming a light reflective diaphragm structures on the first sacrificial layer; forming fiber stopper structures on the light reflective diaphragm structures; forming fiber alignment cavity structures on the fiber stopper structures, the light reflective diaphragm structures, fiber stopper structures and fiber alignment cavity structures providing a plurality of fiber alignment assemblies; providing a second substrate with a second sacrificial layer formed thereover; forming ferrule structures over the second sacrificial layer; inputting fibers into the ferrule structures and sealing each of the ferrule structures to the fiber inserted therein, the ferrule structures and the fibers providing fiber-ferrule assemblies; etching the second sacrificial layer releasing the fiber-ferrule assemblies; inputting the fiber-ferrule assemblies into the fiber alignment assemblies and sealing each of the fiber alignment assemblies to the fiber-ferrule assembly inserted therein, the fiber alignment assemblies and the fiber-ferrule assemblies providing a plurality of fiber optic pressure transducers; and etching the first sacrificial layer releasing the fiber optic pressure transducers.

In an preferred embodiment, the light reflective diaphragm structures are formed from a photosensitive polymer, a non-photosensitive polymer and/or a metal. In an preferred embodiment, the fiber stopper structures, the fiber alignment cavity structures and the ferrule structures are formed from an epoxy-based photoresist.

A method of batch fabrication of ultraminiature fiber optic pressure transducers in accordance with another embodiment of the present invention includes the step of: employing a surface micromachining technique to provide a flexible diaphragm with an integrally formed fiber alignment structure, the fiber alignment structure being sized to receive a fiber-ferrule assembly therein. In a preferred embodiment, the method further includes the step of: employing the surface micromachining technique to fabricate a ferrule structure of the fiber-ferrule assembly, the ferrule structure being sized to receive a fiber of the fiber-ferrule assembly.

A method of batch fabrication of ultraminiature fiber optic pressure transducers in accordance with another embodiment of the present invention includes the step of: employing a surface micromachining technique to provide a flexible diaphragm with an integrally formed fiber stopper structure.

An ultraminiature fiber optic pressure transducer in accordance with another embodiment of the present invention includes: a flexible diaphragm; a fiber alignment structure secured to the flexible diaphragm, the fiber alignment structure being formed with a photosensitive polymer; and a fiber-ferrule assembly sealed within the fiber alignment structure.

An ultraminiature fiber optic pressure transducer system in accordance with another embodiment of the present invention includes: a plurality of ultraminiature fiber optic pressure transducers configured to measure pressures within a plurality of pressure ranges which are different and to generate output signals for the pressure ranges; and a processor configured to receive and process the output signals.

An ultraminiature fiber optic pressure transducer system in accordance with another embodiment of the present invention includes: an ultraminiature fiber optic pressure transducer adapted to generate an output signal; and a transmitter electrically connected to the pressure transducer, the transmitter being adapted to receive and transmit the output signal.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 1 is a cross-sectional view of an exemplary preferred fiber optic pressure transducer according to the present invention;

FIG. 2 is a cross-sectional view showing a portion of a substrate coated with a sacrificial layer of aluminum, an epoxy-based photoresist layer and a second aluminum layer in accordance with an exemplary preferred method of the present invention;

FIG. 3 is a cross-sectional view of the portion of a substrate of FIG. 2 showing the sacrificial layer of aluminum and three mirrored diaphragms formed at one stage of fabrication in accordance with an exemplary preferred method of the present invention;

FIG. 4 is a cross-sectional view of the portion of a substrate of FIG. 3 showing fiber stopper annular structures formed of an epoxy-based photoresist on an upper surface of the substrate and aligned with the mirrored diaphragms in accordance with an exemplary preferred method of the present invention;

FIG. 5 is a cross-sectional view of the portion of a substrate of FIG. 4 showing fiber alignment cavity structures formed of an epoxy-based photoresist on the fiber stopper annular structures in accordance with an exemplary preferred method of the present invention;

DETAILED DESCRIPTION OF THE PREFERRED EMBODIMENTS

Figure 6:
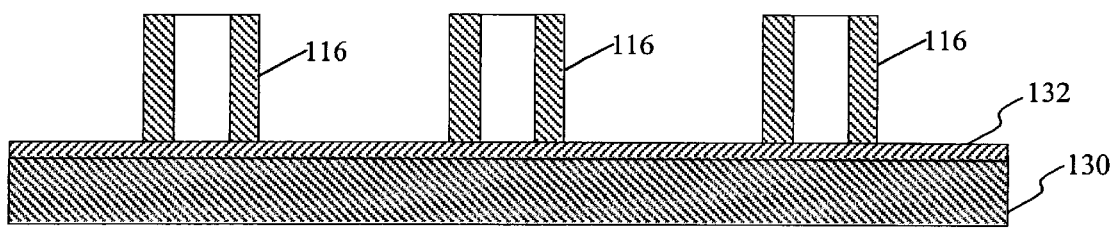
FIG. 6 is a cross-sectional view showing a portion of an additional substrate coated with a sacrificial layer of aluminum and three ferrule structures formed of an epoxy-based photoresist in accordance with an exemplary preferred method of the present invention.

The following is a detailed description of the best presently known mode of carrying out the invention. This description is not to be taken in a limiting sense, but is made merely for the purpose of illustrating the general principles of the invention.

Referring to FIG. 1, an exemplary preferred fiber optic pressure transducer 100 according to the present invention includes a fiber alignment assembly 102 and a fiber-ferrule assembly 104 sealed together with a sealant 106 to provide a transducer cavity 108. The illustrated fiber alignment assembly 102 includes a light reflective diaphragm 110, a fiber stopper 112 and an alignment structure 114. The illustrated fiber-ferrule assembly 104 includes a ferrule 116 and a fiber 118.

The sensitivity of the pressure transducer 100, in general, depends on the stiffness of the diaphragm 110, its surface area, and its thickness. As the diameter of the diaphragm 110 is decreased (with a decrease in the size of the transducer 100, for example), its sensitivity to pressure decreases inversely proportional to the square of the diameter. This sensitivity can be partially compensated for by decreasing the thickness of the diaphragm 110 and utilizing diaphragm materials with low stiffness such as polymers. Another approach to increasing the sensitivity of small sized transducers is to utilize an optic fiber with a small distal end and a high numerical aperture as disclosed in U.S. Pat. No. 5,438,873 to Wlodarczyk et al., the entirety of which is incorporated herein by reference. In addition, sensitivity is dramatically increased if the initial distance between the end of the fiber 118 and the light reflective diaphragm 110 is comparable with the fiber core diameter.

Referring to FIGS. 2–10, an exemplary preferred method for fabricating the pressure transducers 100 is illustrated. Referring to FIG. 2, a substrate 120 is provided with a sacrificial layer 122, a layer 124 of flexible material, and a reflective layer 126 as shown. The thicknesses illustrated in FIG. 2 have been enlarged for purposes of visual clarity.

An exemplary preferred substrate 120 comprises a polished silicon wafer. Materials for the sacrificial layer 122 are selected to provide a sufficient amount of adhesion to the substrate 120 and the layer 124, survive the full fabrication process, and provide etching selectivity with respect to the formed microstructure. An exemplary preferred sacrificial layer 122 comprises an aluminum layer with a thickness of around 200 nm.

The light reflective diaphragm 110 comprises, for example, layer of photosensitive or non-photosensitive polymer 124 coated with a metal layer 126 having a higher reflectivity than the photosensitive or non-photosensitive polymer layer 124 and a sufficient amount of adhesion to the material of the flexible layer 124. An exemplary preferred layer 124 comprises a layer of epoxy-based photoresist such as SU-8 with a thickness of around 1 $\mu$m. An exemplary preferred reflective layer 126 comprises a layer of aluminum with a thickness of around 180 nm. It should be understood that other materials and dimensions can be employed. For example, a layer of polyimide could be used with nonaqueous solutions.

Referring to FIG. 3, the fabrication method of the present invention next provides for formation of a plurality of light reflective diaphragms 110 from the layer 124 and the reflective layer 126. According to an exemplary preferred method, the layer 124 of photosensitive polymer (such as epoxy-based photoresist SU-8) is exposed to a conventional lithographic patterning, cured in a conventional fashion, and then the layer 126 of aluminum is formed thereover. The upper surface of the layer 126 is then provided with a mask by a conventional photoresist technique, and the reflective layer 126 is patterned using a conventional etchant to form the light reflective diaphragms 110 as illustrated.

Referring to FIG. 4, the next step of the fabrication method of the present invention is to form a plurality of the fiber stoppers 112. According to an exemplary preferred method, a photosensitive polymer such as epoxy-based SU-8 is applied to form, by conventional lithography, the fiber stoppers 112 as standing apart cavity structures (having a height of 10 $\mu$m, for example) aligned with the plurality of light reflective diaphragms 110 as shown and sized to receive the ferrules 116 therein. Microstructures of various geometric shapes can be batch fabricated according to the thick photoresist process described by Lorenz, H., et al. in "SU-8: a low-cost negative resist for MEMS", *J. Micromech. Microeng.* 7 (1997), pp. 121–124, which is incorporated herein by reference. A photosensitive polymer such as epoxy-based SU-8 facilitates the formation of high aspect ratio solid microstructures with vertical walls and excellent adhesion to different materials for the purpose of forming mechanical sensing elements for fiber optic pressure transducers.

Referring to FIG. 5, the next step of an exemplary preferred fabrication method according to the present invention is to again apply a photosensitive polymer such as epoxy-based SU-8 to form, by conventional lithography, the alignment structures 114 as standing apart precise cavity structures (having a height of 200 $\mu$m, for example) aligned with the plurality of light reflective diaphragms 110 as shown and sized to receive the ferrules 116 therein. After baking in a conventional fashion, the light reflective diaphragms 110, the fiber stoppers 112 and the alignment structures 114 are ready to serve as fiber alignment structures and integral members of the monolithic pressure sensing elements.

Referring to FIG. 6, the next step of an exemplary preferred fabrication method according to the present invention is to provide an additional substrate 130 with a sacrificial layer 132, and to form a plurality of the ferrule structures 116 thereover. An exemplary preferred substrate 130 comprises a polished silicon wafer. An exemplary preferred sacrificial layer 132 comprises aluminum. The thicknesses illustrated in FIG. 6 have been enlarged for purposes of visual clarity.

Exemplary preferred ferrule structures 116 are formed by coating the aluminum sacrificial layer 132 with a photosensitive polymer such as epoxy-based photoresist SU-8 with a thickness of about 200 $\mu$m (for example) This layer is then patterned and baked in a conventional fashion to form precise fiber ferrule structures 116 sized to receive the fibers 118 therein.

Figure 7:
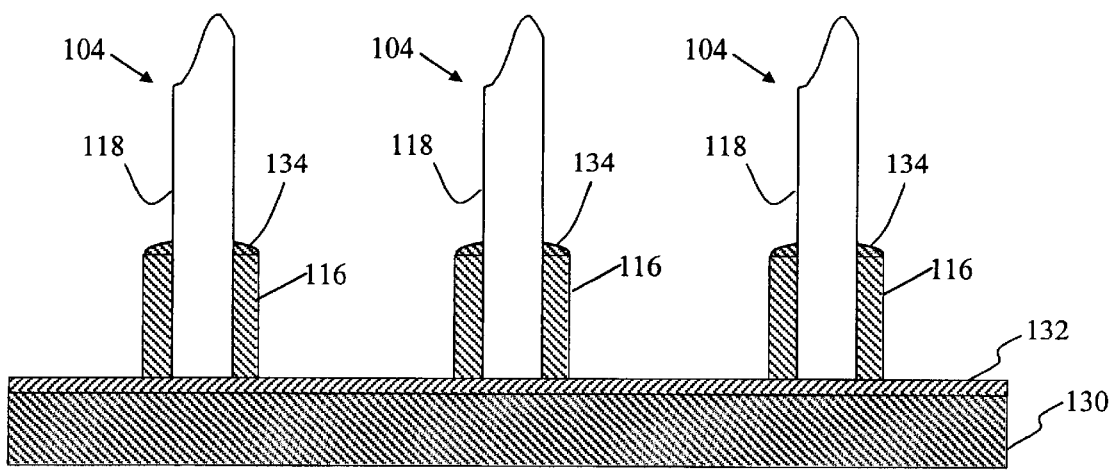
FIG. 7 is a cross-sectional view of the portion of an additional substrate of FIG. 6 showing fibers inputted into the ferrule structures and sealed with adhesive in accordance with an exemplary preferred method of the present invention.

Referring to FIG. 7, the next step of the fabrication method is to insert the fibers 118 into the ferrule structures 116 employing a sealant 134 such as a conventional epoxy to seal the fibers 118 therein. Exemplary preferred fibers 118 comprise single mode fibers with an outer diameter of 125 $\mu$m and a core diameter of about 9 $\mu$m. Single mode fibers of different sizes and multi-mode fibers can also be employed. The fibers 118 can also include a conventional coating for added durability and resistance to bodily fluids.

Figure 8:
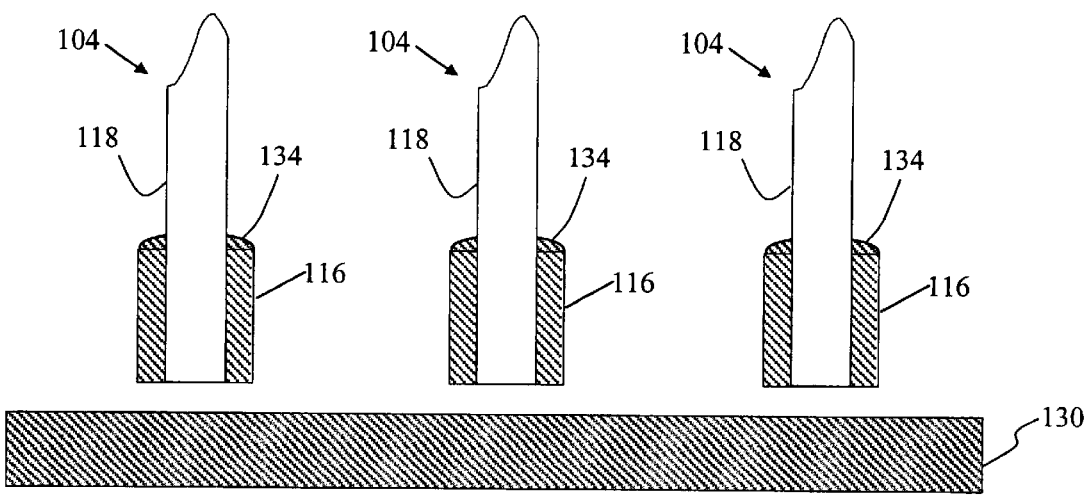
FIG. 8 is a cross-sectional view of the portion of an additional substrate of FIG. 7 showing released fiber-ferrule assemblies after the sacrificial layer of aluminum is etched out in accordance with an exemplary preferred method of the present invention.

Referring to FIG. 8, the next step of the fabrication method is to simultaneously release the sealed fiber-ferrule assemblies 104 by etching away the sacrificial layer 132 with a conventional etchant. During this step, the fiber-ferrule assemblies 104 are held by a conventional holder (not shown).

Figure 9:
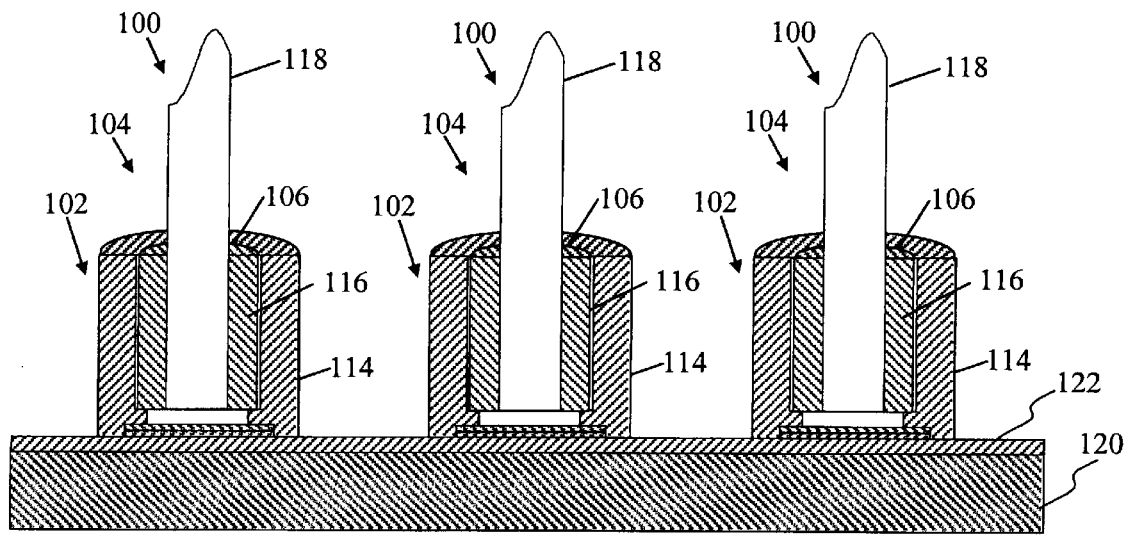
FIG. 9 is a cross-sectional view of the portion of a substrate of FIG. 5 showing the fiber-ferrule assemblies of FIG. 8 inputted into the fiber alignment structures and sealed with adhesive in accordance with an exemplary preferred method of the present invention.

Referring to FIG. 9, the next step of an exemplary preferred fabrication method according to the present invention is to input the fiber-ferrule assemblies 104 into the fiber alignment assemblies 102 employing the holder. The fiber-ferrule assemblies 104 are advanced into the fiber alignment assemblies 102 until the ferrules 116 run into or contact the fiber stoppers 112. The fiber-ferrule assemblies 104 and fiber alignment assemblies 102 are sealed together with the sealant 106 which comprises, for example, a conventional epoxy. By using photoresist SU-8, very tall, solid and precise alignment structures (up to 1 mm, for example) can be built thus facilitating accurate and easy alignment of the fiber-ferrule assemblies 104 with the light reflective diaphragms 110. Moreover, the light reflective diaphragms 110 are protected from being damaged during the insertion of the fiber-ferrule assemblies 104 into the fiber alignment assemblies 102 because the diaphragms 110 remain attached to the sacrificial layer 122 during this assembly process.

Figure 10:
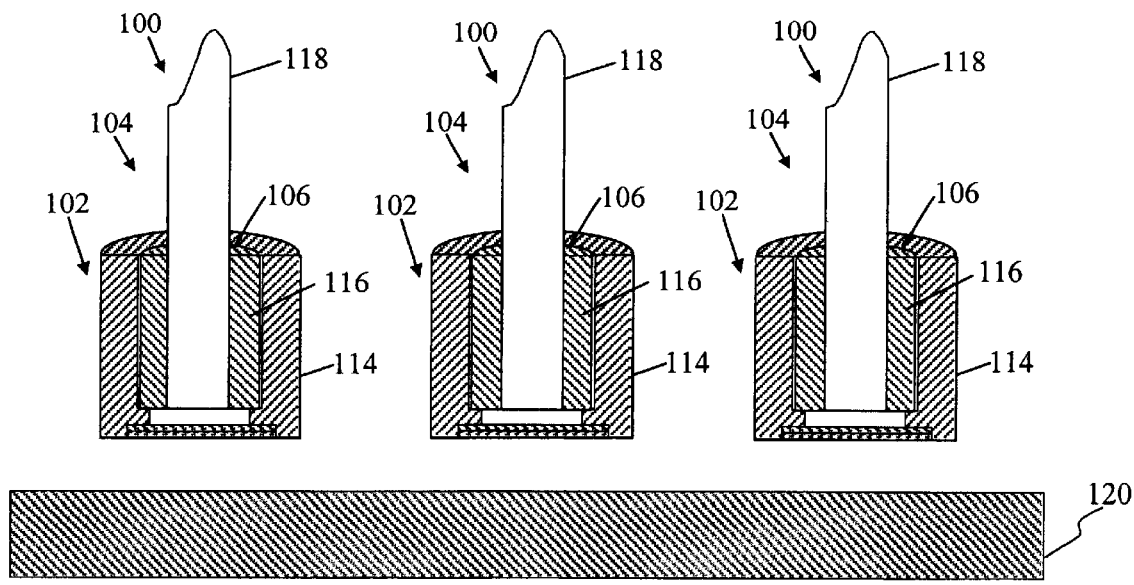
FIG. 10 is a cross-sectional view of the portion of a substrate of FIG. 9 showing released ultraminiature fiber optic pressure transducers after the sacrificial layer is etched out in accordance with an exemplary preferred method of the present invention.

Referring to FIG. 10, the final step of the fabrication method is to simultaneously release the completed fiber optic pressure transducers 100 (which have an outer diameter of 350 $\mu$m, for example) by etching away the sacrificial layer 122 with a conventional etchant. Thus, according to the fabrication method of the present invention, all of the completed pressure transducers 100 are released without having to dice the substrate 120.

The completed pressure transducers 100 can be used individually or in groups, as pressure measuring devices or as components of other devices. By way of example, two of the pressure transducers 100 can be incorporated into a flow meter with pressure being measured at two locations.

Figure 11:
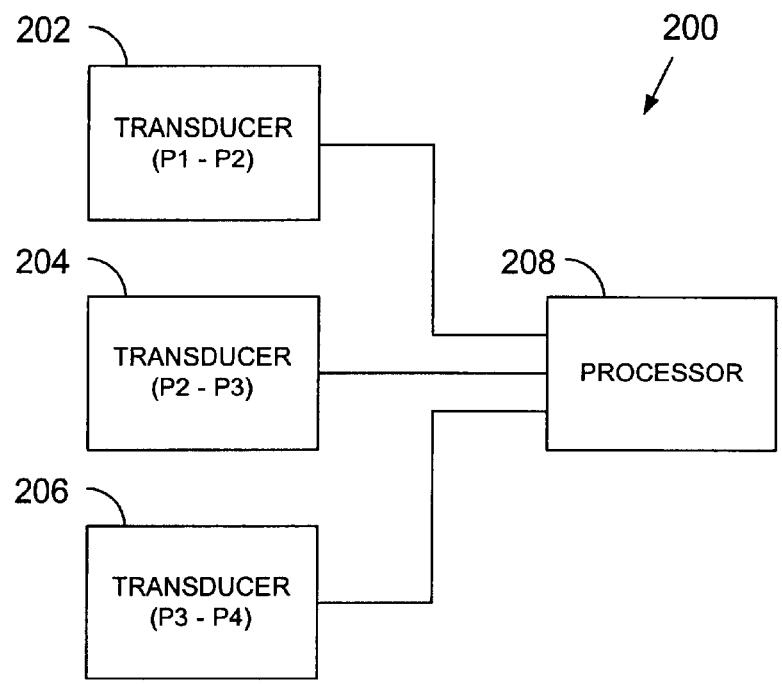
FIG. 11 illustrates an exemplary preferred pressure transducer system including a plurality of ultraminiature fiber optic pressure transducers according to the present invention.

Referring to FIG. 11, an exemplary preferred ultraminiature fiber optic pressure transducer system 200 includes a plurality of ultraminiature fiber optic pressure transducers 202, 204, 206 and a processor 208 electrically connected as shown. Each of the pressure transducers 202, 204, 206 is configured to measure pressure within a different pressure range and to generate output signals for its respective pressure range. The processor 208 is configured to receive and process these output signals.

In the illustrated exemplary preferred embodiment, the pressure transducer 202 is configured to measure pressure within the pressure range P1–P2. The pressure transducer 204, in turn, is configured to measure pressure within the pressure range P2–P3; and the pressure transducer 206 is configured to measure pressure within the pressure range P3–P4. By employing a plurality of pressure transducers to measure different ranges of pressures, greater measuring accuracy can be achieved over a greater range (or ranges) of pressures. Although the illustrated ultraminiature fiber optic pressure transducer system 200 is configured with three pressure transducers which measure contiguous pressure ranges, it should be understood that such a system can employ other quantities and configurations of pressure transducers.

Figure 12:
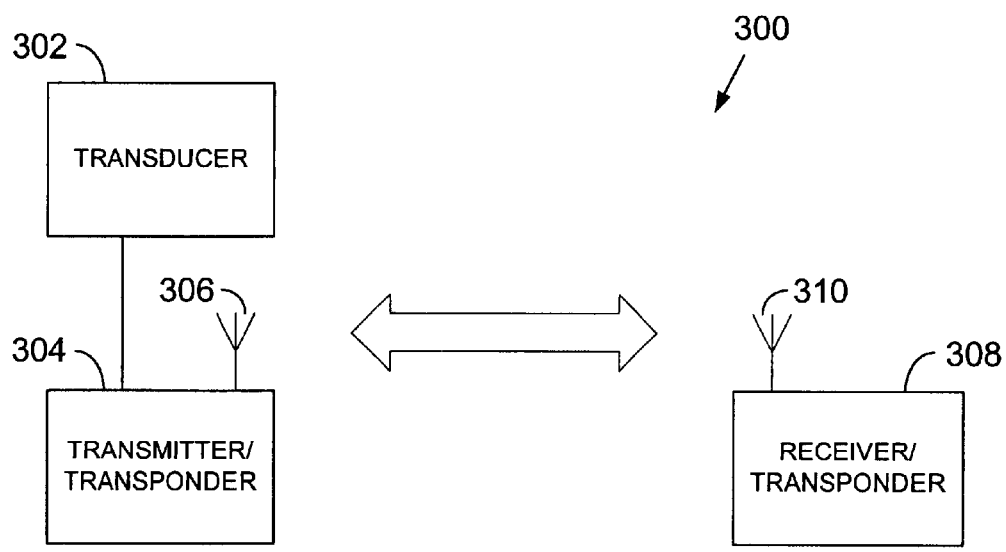
FIG. 12 illustrates an exemplary preferred pressure transducer system including a wireless communications link according to the present invention.

Referring to FIG. 12, an exemplary preferred "wireless" ultraminiature fiber optic pressure transducer system 300 includes an ultraminiature fiber optic pressure transducer 302 and a transmitter/transponder 304 with an antenna 306 electrically connected as shown. The pressure transducer 302 is adapted to generate an output signal; and the transmitter/transponder 304 is adapted to receive and transmit the output signal. Thus, the pressure transducer system 300 provides a wireless communication link between the pressure transducer 302 and a remote receiver unit such as the illustrated receiver/transponder 308 with its antenna 310.

Although the present invention has been described in terms of the preferred embodiments above, numerous modifications and/or additions to the above-described preferred embodiments would be readily apparent to one skilled in the art. For example, the principles of the present invention are generally applicable to the fabrication of MicroElectroMechanical Systems ("MEMS") as well as other small electrical/mechanical devices and micromachine devices. It is intended that the scope of the present invention extend to all such modifications and/or additions.

We claim:

1. A method of batch fabrication of ultraminiature fiber optic pressure transducers, comprising the steps of:
   providing a first substrate with a first sacrificial layer formed thereover;
   forming a plurality of light reflective diaphragm structures on the first sacrificial layer;
   forming a plurality of fiber stopper structures on the light reflective diaphragm structures;
   forming a plurality of fiber alignment cavity structures on the fiber stopper structures, the light reflective diaphragm structures, fiber stopper structures and fiber alignment cavity structures providing a plurality of fiber alignment assemblies;
   providing a second substrate with a second sacrificial layer formed thereover;
   forming a plurality of ferrule structures over the second sacrificial layer;
   inputting a plurality of fibers into the ferrule structures and sealing each of the ferrule structures to the fiber inserted therein, the ferrule structures and the fibers providing a plurality of fiber-ferrule assemblies;
   etching the second sacrificial layer releasing the fiber-ferrule assemblies;
   inputting the fiber-ferrule assemblies into the fiber alignment assemblies and sealing each of the fiber alignment assemblies to the fiber-ferrule assembly inserted therein, the fiber alignment assemblies and the fiber-ferrule assemblies providing a plurality of fiber optic pressure transducers; and
   etching the first sacrificial layer releasing the fiber optic pressure transducers.

2. A method as claimed in claim 1 wherein the sacrificial layers comprise a metal.

3. A method as claimed in claim 1 wherein the light reflective diaphragm structures are formed from a group of materials consisting of a photosensitive polymer, a non-photosensitive polymer, and a metal.

4. A method as claimed in claim 1 wherein the fiber stopper structures are formed from a photosensitive polymer.

5. A method as claimed in claim 1 wherein the fiber stopper structures are formed from a metal.

6. A method as claimed in claim 1 wherein the fiber alignment cavity structures are formed from a photosensitive polymer.

7. A method as claimed in claim 1 wherein the ferrule structures are formed from a photosensitive polymer.

8. A product resulting from the method of claim 1 wherein the product is a fiber optic pressure transducer.

9. A product resulting from the method of claim 1 wherein the product is a pressure sensing element.

10. A product resulting from the method of claim 1 wherein the product is a fiber stopper structure.

11. A product resulting from the method of claim 1 wherein the product is a fiber alignment structure.

12. A product resulting from the method of claim 1 wherein the product is a fiber-ferrule assembly.

* * * * *